United States Patent [19]

Farber

[11] 4,026,883
[45] May 31, 1977

[54] DERIVATIVES OF DIANHYDRIDES AS VINYL COLOR FORMERS

[75] Inventor: Sheldon Farber, Appleton, Wis.

[73] Assignee: NCR Corporation, Dayton, Ohio

[22] Filed: Apr. 10, 1975

[21] Appl. No.: 567,024

[52] U.S. Cl. .............................. 260/240 D; 106/19; 106/21; 260/240.3; 260/295 B; 260/295 F; 260/295 T; 260/315; 260/326.14 R; 260/326.25; 260/326.27; 260/326.34; 260/343.3
[51] Int. Cl.² .......................................... C09B 23/00
[58] Field of Search ........ 260/343.3, 295 T, 295 F, 260/240 D

[56] References Cited
UNITED STATES PATENTS 3,491,117   1/1970   Lin ........................... 260/326.14 R

OTHER PUBLICATIONS

Chem. Abstracts 83:10978c.
Chem. Abstracts 54:8422c.

*Primary Examiner*—Ethel G. Love
*Attorney, Agent, or Firm*—E. Frank McKinney

[57] ABSTRACT

A chromogenic compound of normally colorless form is disclosed having the following structural formula:

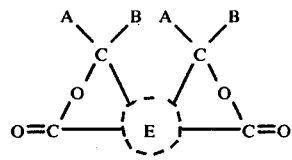

wherein
A and B can be

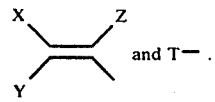
and T—.

T, X, Y and Z can be, among several others, hydrogen, alkyl, alkoxy, aryl, and heterocyclic, substituted and unsubstituted; and E can be a broad family of aromatic and heterocyclic structures. The compound is eligible for use in pressure-sensitive record materials and manifold marking systems. Because of light absorption characteristics, selected compounds of this invention are especially useful where machine readability and machine copiability are important.

12 Claims, 1 Drawing Figure

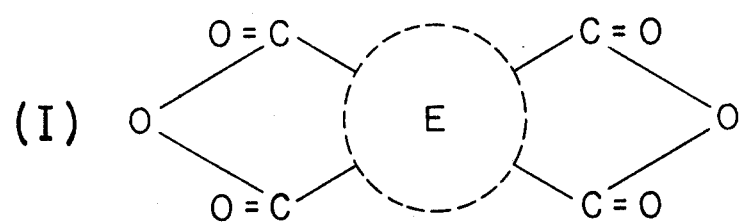
(I)
(A) 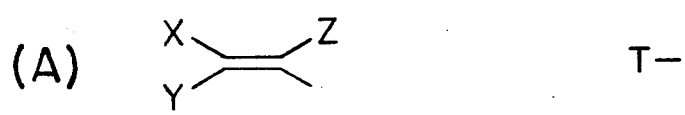 T—
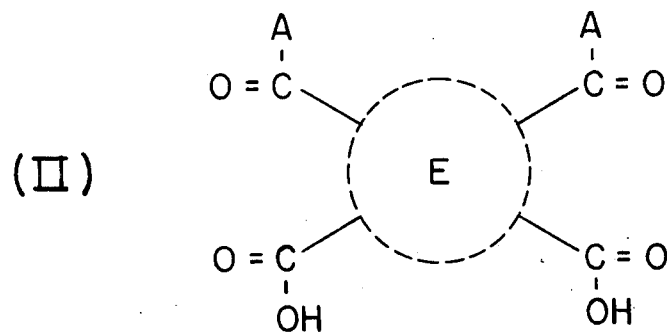
(II)
(B) 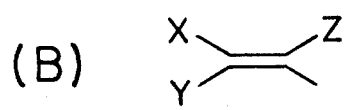
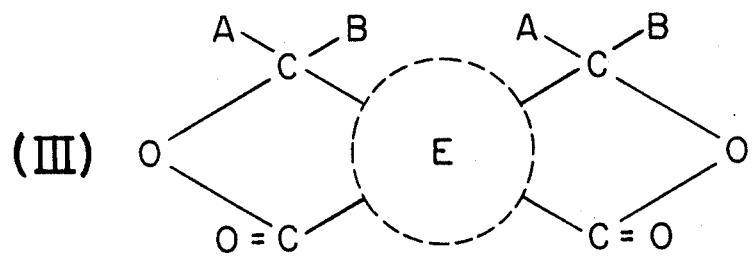
(III)

DERIVATIVES OF DIANHYDRIDES AS VINYL COLOR FORMERS

BACKGROUND OF THE INVENTION

1. Field of the Invention

This invention pertains to colorable chromogenic compounds eligible for use in pressure-sensitive record material. Pressure-sensitive mark-forming record systems, single sheet and manifold, are improved by use of these compounds.

More specifically, this invention relates to chromogenic compounds having at least two vinyl linkages which compounds have the form of substantially colorless or slightly colored solids, or which approach being colorless when in liquid solution; but, which may be converted to dark-colored forms upon reactive contact with acidic material. As used in mark-forming systems, marking in desired areas on support webs or sheets may be accomplished by effecting localized reactive contact between the chromogenic material and the acidic material on or in such web or sheet;--such material being brought thereto by transfer, or originally there, in situ, the desired reactive contact forming darkcolored materials in the intended image-marking areas.

The chromogenic compounds of this invention have the following general formula:

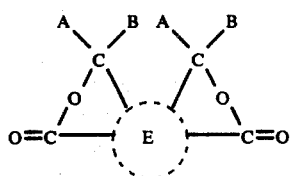

wherein
A and B can be

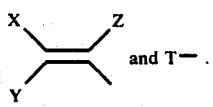

T, X, Y, and Z can be, among several others, hydrogen, alkyl, alkoxy, aryl, and heterocyclic, substituted and unsubstituted; and E can be a broad family of aromatic and heterocyclic structures.

The chromogenic compounds of this invention especially relate to marks at or near the near infrared part of the color spectrum; and, in that regard, especially relate to providing a color which is particularly visible to machine readers and copiers.

2. Description of the Prior Art

Several phthalide and fluoran chromogenic compounds have been disclosed. For example, U.S. Pat. Nos. 3,491,111, and 3,491,116, issued Jan. 20, 1970, disclose indol- and carbazol-substituted phthalides, U.S. Pat. No. 2,417,897, issued Mar. 25, 1947, discloses crystal violet lactone. U.S. Pat. No. 3,681,390, issued Aug. 1, 1972, discloses aryl-substituted fluorans.

U.S. Pat. No. 3,672,935, issued June 27, 1972, discloses use of colorless chromogenic compounds in pressure-sensitive record material.

G. Hallas, in the *Journal of the Society of Dyers and Colourists*, in September, 1967, at pages 368 to 373 and in June, 1970 at pages 237–242 discusses the effects of extended conjugation on colored dye compounds.

SUMMARY OF THE INVENTION

Colorable chromogenic compounds having at least two vinyl linkages have been discovered which compounds are initially substantially colorless but produce dark-colored products on reaction with certain acid materials. The vinyl-containing chromogenic compounds exhibit light absorption, in the colored form, at wavelengths nearer to infrared than chromogenic compounds without vinyl groups. It is an object of this invention to provide such vinyl-containing compounds and methods for making them.

An important use for the vinyl compounds of this invention resides in their incorporation into pressure-sensitive record systems as a colorable reactant for development of color on application of a mark-forming force. Hence, it is an object of this invention to provide substances having near infrared color response and chromogenic properties, which substances can be incorporated in a web or coated onto the surface of a web to provide a record sheet or a manifolding unit, and which are useful in carrying out methods of marking involving a reactive contact with a color-activating material to develop dark-colored materials in areas where marking is desired.

It is an object of this invention to provide modified compounds, based upon the aforementioned vinyl-containing compounds, which are substantially colorless, or slightly colored, offering a variety of chromogenic characteristics, and developing dark-colored substances absorbing at increased wavelengths upon contact with color-activating materials.

BRIEF DESCRIPTION OF THE DRAWING

The chromogenic compounds of this invention include a large variety of several moieties with the vinyl linkages and lactone rings being necessarily common to all. In order to more completely and more distinctly disclose the variety of moiety combinations which forms a part of this invention, a drawing is included which is a schematic representation of the combination, by structural formula.

The drawing represents a figurative, schematic, step-by-step structural development of the vinyl-containing compounds of this invention, as they can be prepared. A dicarboxylic dianhydride (I) is combined with a substrate reactant (A) to yield a keto acid (II), vinyl-containing or not, which is, in turn, combined with a vinyl-containing substrate reactant (B) to yield the chromogenic (III) of this invention. The structural development shown is not necessarily a representation of the actual compound synthesis. For example, in preparing tetravinyl compounds of this invention, wherein (A) is vinyl-containing, the reaction does not necessarily go through separate and individual steps, as shown; and, in fact, the keto acid (II) may have only a fleeting existence, if it exists at all. The synthetic process is not embraced as a part of this invention.

The dicarboxylic dianhydride (I), in the FIGURE, includes E as the supporting molecular structure. E represents a large variety of structures including aromatic and heterocyclic, substituted and unsubstituted. The substitutions include halo, nitro, cyano, and alkylthio, alkoxy, alkyl, monoalkylamino, and dialkylamino with alkyl of less than seven carbon atoms. Halogen or halo-, in this invention, means fluorine, chlorine, bromine and iodine, (I) is not required to be a dicarboxylic dianhydride. A dicarboxylic acid will suffice if the keto acid-forming reaction is conducted under dehydrating conditions such as in acetic anhydride. Moreover, the vinyl-containing compounds (A) and (B) can be a methyl carbinol under dehydrating conditions.

(A) and (B) provide structural, schematic, indication of the manner in which vinyl linkages are introduced into the compounds of this invention. While there are differences between the specific moieties which will be disclosed in detail, below, it suffices to say, here, that T, X, Y and Z represent, among other things, substituted and unsubstituted aromatic and heterocyclic groups as a part of the moieties of (A) and (B).

DETAILED DESCRIPTION OF THE INVENTION

It should be remembered that what is considered to be an essential element of the invention herein is the presence of at least two vinyl linkages in a colorless but colorable chromogenic material. At the present time, the chromogenic compounds of this invention enjoy extensive eligibility for use in pressure-sensitive and thermally-sensitive mark-forming systems. Pressure-sensitive mark-forming systems provide a marking system of disposing on and/or within sheet support material unreacted mark-forming components and a liquid solvent in which each of the mark-forming components is soluble, said liquid solvent being present in such form that it is maintained isolated by a pressure-rupturable barrier, from at least one of the mark-forming components until application of pressure causes a breach of the barrier in the area delineated by the pressure pattern. The mark-forming components are thereby brought into reactive contact, producing a distinctive mark.

The method of marking comprises providing a chromogenic compound selected from among the above-mentioned compounds and bringing such chromogenic compound into reactive contact, in areas where marking is desired, with an acidic color-activating substance to produce a dark-colored form of the chromogenic compound.

The acidic materials can be any compound within the definition of a Lewis acid, i.e., an electron acceptor. Preferably, acidic organic polymers such as phenolic polymers are employed as the acidic material. It is noted that the polymeric mark-forming components should have a common solubility with the chromogenic compound in at least one liquid solvent when the acid-reacting material is a phenolic or other organic acidic polymer. It is noted that in a single system several chromogenic compounds can be used with the same or different polymeric materials. Several polymeric materials can be reactively contacted with a single chromogenic compound or with a mixture of chromogenic compounds.

The acidic polymeric material useful in this invention includes phenol polymers, phenol acetylene polymers, alkyl-phenol-acetylene polymers, maleic acid-rosin resins, partially or wholly hydrolyzed styrene-maleic anhydride copolymers and ethylene-maleic anhydride copolymers, carboxy polymethylene and wholly or partially hydrolyzed vinyl methyl ether maleic anhydride copolymers and mixtures thereof.

When the acidic material is one of the aforementioned organic polymers, the liquid solvent chosen must be capable of dissolving the mark-forming components. The solvent can be volatile or non-volatile, and a single or multiple component solvent may be used which is wholly or partially volatile. Examples of volatile solvents useful in the aforedescribed basic chromogen-acidic polymer are toluene, petroleum distillate, perchloroethylene, and xylene. Examples of non-volatile solvents are high-boiling point petroleum fractions, dioctyl adipate, biphenyls, diphenyl alkanes, and the like.

Generally, the solvent chosen should be capable of dissolving at least 0.3 percent, by weight, of the chromogenic compounds and at least about 3–5 percent, by weight, of the polymeric material. A further criterion of the solvent is that it must not interfere with the mark-forming reaction.

The support member on which the components of the system are disposed may comprise a single or dual sheet assembly. In the case where all compounds are disposed on a single sheet surface, the record material is referred to as a "self-contained" system. Where there must be a migration of the solvent, with or without mark-forming component, from one sheet to another, the record material is referred to as a "transfer" system. (Such a system can also be referred to as a "two-fold" system, in that at least two sheets are required and each sheet includes a component, or components, essential to the mark-forming reaction.) Where a copious amount of the colored reaction product in liquid form is produced on a surface of one sheet, it can produce a mark by transfer to a second sheet as a colored mark.

The polymeric material can be dissolved in ink composition vehicles to form a printing "ink" of colorless character and, thus, can be used to spot-print a proposed record sheet unit sensitized for recording in a reaction-produced color in those areas by application of a solution of the chromogenic material. In the case of phenolic polymer, a printing ink can be made of up to 75 percent, by weight, of the phenolic polymeric material in a petroleum solvent to a viscosity suitable for printing purposes.

In the mark-forming system herein, the acidic mark-forming component(s) reacts with the chromogenic material(s) to effect distinctive color formation or color change. In a multi-sheet system in which an acid organic polymer is employed, it is desirable to include other materials to supplement the reactants. For example, kaolin can be added to improve the transfer of the liquid and/or the dissolved materials between the sheets. In addition, other materials such as bentonite, attapulgite, talc, feldspar, halloysite, magnesium trisilicate, silica gel, pyrophyllite, zinc sulfide, calcium sulfide, calcium citrate, calcium phosphate, calcium fluoride, barium sulfate and tannic acid can be included. It should be noted that mineral materials such as kaolin, attapulgite, silica gel, silton clay, and the like can, also, be used alone or in combination with other materials as an acidic material coreactant.

Various methods known to the prior art and disclosed in the aforementioned U.S. Pat. No. 3,672,935 can be employed in coating compositions of the mark-forming materials into their supporting sheets. An example of the compositions which can be coated onto the surface of an underlying sheet of a two-sheet system to react with the chromogenic material on the underside of any overlying sheet is as follows:

| Coating Composition | Percent by Weight |
| --- | --- |
| Phenolic polymer mixture | 17 |
| Paper coating kaolin (white) | 57 |

-continued

| Coating Composition | Percent by Weight |
|---|---|
| Calcium carbonate | 12 |
| Styrene butadiene latex | 4 |
| Ethylated starch | 8 |
| Gum arabic | 2 |
| | 100 |

Thermally-sensitive mark-forming systems can also be prepared using the compounds of this invention.

The compounds of this invention can be prepared to be symmetrical or not as will be discussed in the examples which follow. Referring, again, to the FIGURE;—E can be the following:

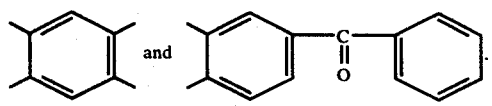

X can be the following:

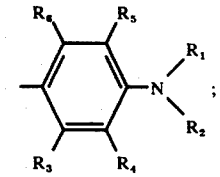

T can be the following:

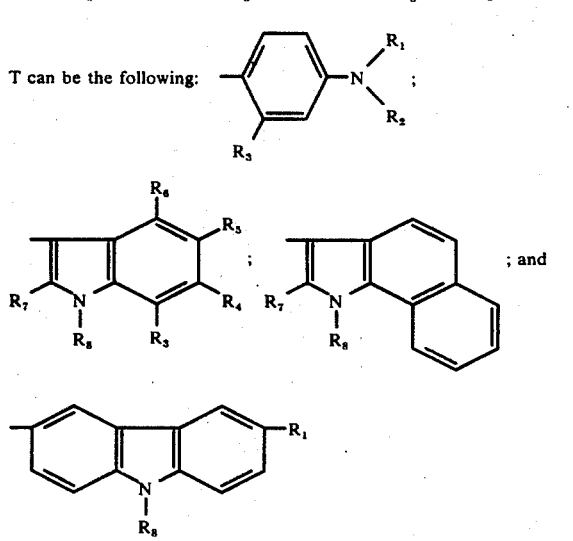

wherein $R_1$ and $R_2$ are hydrogen, alkyl, substituted phenyl, unsubstituted phenyl, benzyl, cycloalkyl, and acyl; $R_3$, $R_4$, $R_5$ and $R_6$ are hydrogen, alkyl, aryl, alkoxy, halo, aralkyl, dialkylamino, monoalkylamino, amino, acylamino, mercapto, and alkylthio; and $R_7$ and $R_8$ are hydrogen, phenyl and alkyl. $R_1$ and $R_2$ are not both phenyl.

Y can be any X and hydrogen.

Z can be hydrogen and methyl when A is vinyl-containing and hydrogen, alkyl, carbalkoxy, benzyl, unsubstituted phenyl, substituted phenyl, pyridino, and halo when A is T.

It should be understood that "alkyl" and any group requiring alkyl, such as "alkoxy" or "dialkylamino" means methyl, ethyl, propyl (including isopropyl), butyl (including isobutyl and tert-butyl), pentyl (including all five-carbon isomers), hexyl (including all six-carbon isomers), and the like having less than 7 carbon atoms.

This invention is further illustrated by the following examples. The reactants and the proportions and other specific conditions are represented as being typical and should not be construed to limit the invention.

DESCRIPTION OF THE PREFERRED EMBODIMENTS

In the following examples, general procedures for preparing certain compounds of this invention are disclosed; and the procedures are followed by summaries of additional compounds prepared in similar manner. The summaries are not intended to be exhaustive and it must be remembered that the moieties, as previously defined, are all eligible for use in any combination in preparing the compounds.

EXAMPLE 1

Preparation of tetra-vinyl chromogenic compounds based on 3,3',4,4'-benzophenonetetracarboxylic dianhydride.

In this example, 3,3',4,4'-benzophenonetetracarboxylicdianhydride (I) and bis-1,1-(dimethylaminophenyl)ethylene (A and B) are reacted together, in acetic anhydride, to yield the chromogenic compound (III) resulting from 3,3',4,4'-benzophenonetetracarboxylicdianhydride with a disubstitution of the ethylene material. The colorless compound imparts a blue color to paper coated with a phenolic or silton clay or a combination of the two. A reflectance spectrum of the blue color has an absorption peak at 875 nanometers.

To prepare a chromogenic compound for this example, approximately two mols each of (A) and (B) are required for each mol of (I). For instance, one mol of 3,3',4,4'-benzophenonetetracarboxylicdianhydride (I) is reacted with four mols of any of the vinyl compounds (A) and (B) previously disclosed or listed below.

Specific examples of eligible vinyl compounds (A) and (B) are as follows:
bis-1,1-(p-dimethylaminophenyl)ethylene;
bis-1,1-(p-diethylaminophenyl)ethylene;
2-methyl-bis-1,1-(p-dimethylaminophenyl)ethylene;
1-(p-dimethylaminophenyl)-1-(methoxyphenyl)ethylene;
1-(p-dimethylaminophenyl)-1-(nitrophenyl)ethylene;
bis-1,1-(p-dibutylaminophenyl)ethylene;
p-dibutylaminophenylethylene;
bis-1,1-(pyrrol-3-yl)ethylene;
bis-1,1-(pyrrol-2-yl)ethylene;
bis-1,1-(indol-3-yl)ethylene;
bis-1,1-(2-methyl-4-dimethylaminophenyl)ethylene;
bis-1,1-(2-ethoxy-4-dimethylaminophenyl)ethylene;
p-dimethylaminophenylethylene;
1-(p-dimethylaminophenyl)-1-(pentoxyphenol)ethylene;
p-di-t-butylaminophenylethylene;
bis-1,1-(2-butoxy-4-dimethylaminophenyl)ethylene;
bis-1,1-(2-dimethylamino-4-diethylaminophenyl)ethylene;
bis-1,1-(2-methylamino-4-dimethylaminophenyl)ethylene;

bis-1,1-(2-amino-4-dimethylaminophenyl)ethylene;
bis-1,1-(2-acetamino-4-dimethylaminophenyl)ethylene; and the like.

EXAMPLE 2

Preparation of tetra-vinyl chromogenic compounds based on pyromellitic dianhydride In this example, pyromellitic dianhydride (I) and bis-1,1-(dimethylaminophenyl)ethylene (A and B) are reacted together, in acetic anhydride, to yield the chromogenic compound (III) resulting from pyromellitic dianhydride with a disubstitution of the ethylene material. The colorless compound imparts a blue color to paper coated with a phenolic resin or silton clay or a combination of the two. A reflectance spectrum of the blue color has an absorption peak at 890 nanometers.

To prepare a chromogenic compound for this example, approximately two mols each of (A) and (B) are required for each mol of (I). For instance, one mol of pyromellitic dianhydride (I) is reacted with four mols of any of the vinyl compounds (A) and (B) previously disclosed.

EXAMPLE 3

Preparation of double mono-vinyl chromogenic compounds

In this example, 3,3',4,4'-benzophenonetetracarboxylicdianhydride (I) and 1-ethyl-2-methylindol (A) are reacted together to yield the keto acid (II). The keto acid (II) is then reacted, in acetic anhydride, with bis-1,1-(dimethylaminophenyl)ethylene (B) to yield the chromogenic compound (III). The colorless compound imparts a bluish-green color to paper coated with a phenolic or silton clay or a combination of the two. A reflectance spectrum of the bluish-green color has an absorption peak of 670 nanometers.

To prepare a chromogenic compound for this example, approximately two mols of the (A) moiety, designated as T —, are required for each mole of (I) to yield the keto acid (II); and approximately two mols of a vinyl compound (B) to yield the final compound (III).

Examples of eligible vinyl compounds are given in Example 1, above. Examples of eligible T — compounds are as follows:
diethylaminophenyl;
dimethylaminophenyl;
2-methoxy-4-diethylaminophenyl;
2-butoxy-4-diethylaminophenyl;
2-methoxy-4-cyclohexylaminophenyl;
phenylaminophenyl;
benzylaminophenyl;
aminophenyl;
2-hexyl-4-dihexylaminophenyl;
2-chloro-4-diethylaminophenyl;
2-phenyl-4-dimethylaminophenyl;
2-dimethylamino-4-diethylaminophenyl;
2-butylamino-4-dimethylaminophenyl;
2-amino-4-dimethylaminophenyl;
2-acetamino-4-dimethylaminophenyl;
2-bromo-4-dimethylaminophenyl;
2-methyl-4-diethylaminophenyl;
2-ethoxy-4-dimethylaminophenyl;
2-hexoxy-4-dimethylaminophenyl;
1-ethyl-2-methylindolyl;
2-phenylindolyl;
1-phenyl-2-methylindolyl;
1-ethyl-2-methyl-5-hexoxyindolyl;
1-hexyl-2-ethylindolyl;
1-ethyl-2-methyl-1H-benz[g]indolyl.

Pyromellitic dianhydride is substituted, in mol equivalents, for the benzophenone dianhydride, used above, to prepare another double mono-vinyl chromogenic compound of this invention.

What is claimed is:
1. A compound having at least two vinyl linkages and represented by the formula:

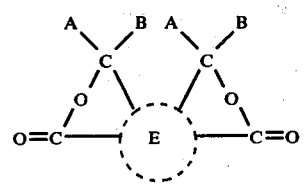

Wherein
E is:

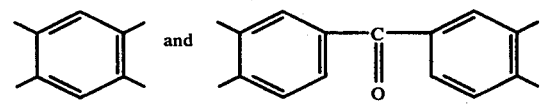

A is:

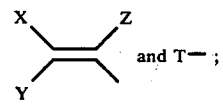

B is:

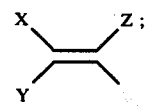

X is:

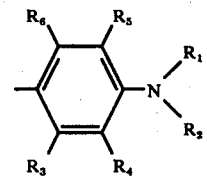

Y is: X and hydrogen;
T is:

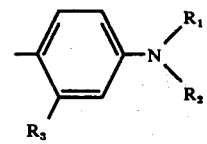

Z is: hydrogen, and methyl when A is

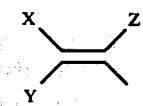

and hydrogen, alkyl, carbalkoxy, benzyl, unsubstituted phenyl, and halo when A is T;

$R_1$ and $R_2$ are: hydrogen, alkyl, unsubstituted phenyl, benzyl and cycloalkyl; but $R_1$ and $R_2$ are not both phenyl;

$R_3$, $R_4$, $R_5$, and $R_6$ are: hydrogen, alkyl, phenyl, benzyl, alkoxy, halo, dialkylamino, monoalkylamino, amino; and $R_7$ and $R_8$ are: hydrogen, phenyl and alkyl.

2. The compound of claim 1 wherein A and B are

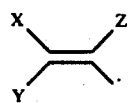

3. The compound of claim 2 wherein X, and Y are

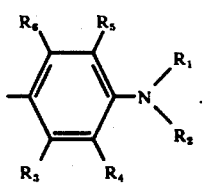

4. The compound of claim 2 wherein X is

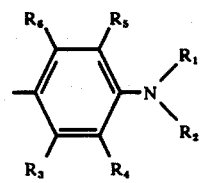

Y is hydrogen.

5. The compound of claim 3 wherein $R_1$ and $R_2$ are alkyl and $R_3$, $R_4$, $R_5$, $R_6$ and Z are hydrogen.

6. The compound of claim 3 wherein $R_1$, $R_2$ and $R_3$ are alkyl and $R_4$, $R_5$, $R_6$ and Z are hydrogen.

7. The compound of claim 4 wherein $R_1$ and $R_2$ are alkyl and $R_3$, $R_4$, $R_5$, $R_6$ and Z are hydrogen.

8. The compound of claim 1 wherein A is T.

9. The compound of claim 8 wherein $R_1$ and $R_2$ are alkyl.

10. The compound of claim 1 wherein Y is X.

11. The compound of claim 10 wherein A is T.

12. The compound of claim 11 wherein
E is:

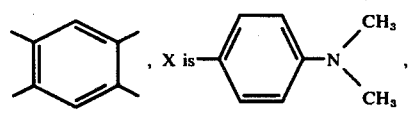

Z is hydrogen, and
T is:

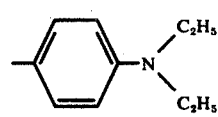

* * * * *